United States Patent [19]

Chauvin et al.

[11] 4,362,650

[45] Dec. 7, 1982

[54] CATALYST AND PROCESS FOR OLEFIN OLIGOMERIZATION

[75] Inventors: Yves Chauvin, Le Pecq; Dominique Commereuc, Meudon; Gérard Leger, Saint Genis les Ollieres; Jean Gaillard, Lyons; Nhu H. Phung, Antony, all of France

[73] Assignee: Institut Francais du Petrole, Rueil-Malmaison, France

[21] Appl. No.: 261,819

[22] Filed: May 8, 1981

[30] Foreign Application Priority Data

May 8, 1980 [FR] France .................................. 80 10359

[51] Int. Cl.$^3$ ......................... B01J 31/04; B01J 31/14
[52] U.S. Cl. .............................. 252/431 C; 585/512; 585/513; 252/429 B
[58] Field of Search ....................... 252/431 C, 429 B

[56] References Cited

U.S. PATENT DOCUMENTS

| | | | |
|---|---|---|---|
| 3,728,283 | 4/1973 | Chauvin et al. | 252/431 C X |
| 3,928,303 | 12/1975 | Yasui et al. | 252/431 C X |
| 3,937,745 | 2/1976 | Wideman et al. | 252/431 C X |
| 4,283,305 | 8/1981 | Chauvin et al. | 252/431 C |

*Primary Examiner*—Patrick Garvin
*Attorney, Agent, or Firm*—Millen & White

[57] ABSTRACT

An improved catalyst composition is obtained by contacting at least one bivalent nickel compound with at least one hydrocarbyl aluminum halide, at least one Bronsted organic acid and at least one anhydride of a carboxylic acid. The composition can be used as a catalyst for olefin oligomerization.

13 Claims, No Drawings

CATALYST AND PROCESS FOR OLEFIN OLIGOMERIZATION

BACKGROUND OF THE INVENTION

The present invention relates to an improved catalytic composition and its use as an oligomerization catalyst, particularly as a dimerization or trimerization catalyst, for monoolefins. The invention more specifically concerns certain compositions obtained by contacting, in any order, at least one bivalent nickel compound with at least one hydrocarbyl aluminum halide, at least one Bronsted organic acid and at least one anhydride of a carboxylic acid.

It is already known to prepare catalysts for dimerizing or co-dimerizing monoolefins such as ethylene, propylene or n-butenes, particularly by reacting bivalent nickel carboxylates with hydrocarbyl aluminum halides. The use of these catalysts is however sometimes objectionable since, in continuous operations, the activity is often lower than in batch operations and this activity also tends to decrease in the course of time.

A first improvement has been obtained by associating a bivalent nickel compound with a hydrocarbyl aluminum halide and a compound having Bronsted acid properties, as disclosed in the published French patent application No. 2 443 877, corresponding to U.S. Pat. No. 4,283,305.

SUMMARY OF THE INVENTION

It has now surprisingly been found, and this is an object of the present invention, that the addition of an anhydride of carboxylic acid to the above association of a bivalent nickel compound with a hydrocarbyl aluminum halide and a compound having Bronsted acid properties leads to a catalytic composition which is more active than the association of the above three compounds: the total amount of catalytic composition necessary to obtain a given conversion rate of the olefins is lower and the proportion of hydrocarbyl aluminum halide can be decreased with respect to the amount of nickel compound.

DETAILED DISCUSSION

The nickel compound may consist of one or more bivalent nickel compounds of any type, preferably those having a solubility of at least 1 g per liter in a hydrocarbon medium (for example in n-heptane at 20° C.), and more particularly in the reactants or the reaction medium, preferably carboxylates of the general formula $(RCOO)_2$ Ni wherein R is hydrocarbyl, for example alkyl, cycloalkyl, alkenyl, aryl, aralkyl or alkaryl having up to 20 carbon atoms, preferably a hydrocarbyl group having from 5 to 20 carbon atoms. The two radicals R may also constitute an alkylene group, having preferably from 6 to 18 carbon atoms. The following bivalent nickel salts are examples of nickel compounds: octoate, 2-ethyl hexanoate, decanoate, stearate, oleate, salicylate, acetylacetonate, hydroxydecanoate. Many other examples can be found in the literature and the patents and the invention is not limited to the sole examples given above. The radical R may be substituted with 1 to 4 or more halogen atoms, hydroxy, ketone, nitro, cyano groups or other groups which do not impede the reaction.

The hydrocarbyl aluminum halides are of the general formula $AlR_xX_y$ wherein R is a hydrocarbon group having, for example, up to 12 carbon atoms, such as alkyl, aryl, aralkyl or cycloalkyl; X represents halogen, F, Cl, Br, I and x has a value from 1 to 1.5, y a value from 1.5 to 2, with $x+y=3$; preferably $x=1$ and $y=2$. Examples of these compounds are ethyl aluminum sesquichloride, dichloroethylaluminum and dichloroisobutylaluminum.

The Bronsted acid is a compound of the formula HX, wherein X is an organic anion, for example a carboxylic, sulfonic or phenolic anion. The acids having a pKa at 20° C. of at most 3 are preferred, particularly those soluble in the nickel compound or in its solution in a hydrocarbon or other appropriate solvent, at the desired concentration, and which do not contain phosphorus. A preferred group of acids includes the halogenocarboxylic acids of the formula $R_1COOH$, wherein $R_1$ is a haloalkyl radical, particularly those having at least one halogen atom in $\alpha$ to the COOH group, with a total of 2 to 10 carbon atoms. A preferred group of acids comprises the halogenocarboxylic acids of the formula $R_1COOH$ wherein $R_1$ is a halogenoalkyl group having from 1 to 3 carbon atoms, of the formula $C_mH_pX_q$, wherein X is halogen, F, Cl, Br, I, m=1, 2 or 3, p is zero or an integer and q is an integer, provided that $p+q=2m+1$. There is preferably used a halogenoacetic acid of the formula $R_2COOH$ wherein $R_2$ is a halogenomethyl radical of the formula $CX_nH_{3-n}$, where X is halogen, F, Cl, Br, I with n being an integer from 1 to 3. In the above formulas, the preferred halogen is F. Useful acids are trifluoroacetic acid, monofluoroacetic acid, trichloroacetic acid, tribromoacetic acid, monobromoacetic acid, triiodoacetic acid, monoiodoacetic acid, pentafluoropropionic acid, 2-fluoropropionic acid, heptafluorobutyric acid or 2-chlorobutyric acid. Other useful acids are, for example, arylsulfonic acids, alkylsulfonic acids, picric acid, nitroacetic acid, nitrobenzoic acid or cyanacetic acid. These examples constitute no limitation.

The anhydride of a carboxylic acid is a compound of the formula $(R_3CO)_2O$ wherein $R_3$ is a hydrocarbon group having up to 20 carbon atoms, preferably 5 to 20 carbon atoms, such as alkyl, aralkyl or cycloalkyl which is—or not—substituted in $\alpha$ of the anhydride group with one or more halogen atoms, F, Cl, Br, I. A preferred group of anhydrides comprises compounds of the formula $(R_2CO)_2O$ wherein $R_2$ is defined as above. Non limitative examples are: octoic, 2-ethyl hexanoic, decanoic, stearic, oleic, trifluoroacetic, monofluoroacetic, trichloroacetic, monochloroacetic, pentafluoropropionic and heptafluorobutyric anhydrides. The $R_2$ and $R_3$ groups forming part of the anhydride formula may be identical (symmetrical anhydrides) or not (dissymmetrical anhydrides).

The invention has also for object a process for oligomerizing monoolefins in the presence of the above catalytic system, at a temperature of $-20°$ C. to $+60°$ C., under such pressure conditions that the reactants are maintained, at least in major part, in liquid or condensed phase.

Monoolefins which can dimerize or oligomerize are, for example, ethylene, propylene, n-butenes, n-pentenes, either pure or as mixtures, such as those obtained by synthesis processes, for example, steam-cracking or catalytic cracking. They can co-dimerize or co-oligomerize as mixtures or with isobutene, for example ethylene with propylene and n-butenes, propylene with n-butenes, n-butenes with isobutene.

The concentration, expressed as nickel, of the catalytic composition in the liquid oligomerization phase is normally between 5 and 200 parts per million by weight. The molar ratio of the hydrocarbyl aluminum halide to the nickel compound is normally from 1:1 to 30:1 and more advantageously from 2:1 to 15:1. The molar ratio of the Bronsted acid to the aluminum compound is from 0.001:1 to 1:1, preferably from 0.01:1 to 0.5:1. The preferred value of the molar ratio of the Bronsted acid to the nickel compound is from 0.25:1 to 5:1. The molar ratio of the anhydride of carboxylic acid to the nickel compound is advantageously from 0.001:1 to 1:1, preferably from 0.01:1 to 0.5:1.

The process can be operated in a reactor with one or more serially arranged reaction stages; the olefinic charge and/or the constituents of the catalytic system are introduced continuously, either into the first stage or into the first and anyone of the stages; or only one, two or three constituents of the catalytic mixture are introduced into the second and/or the $n^{th}$ stage.

When discharged from the reactor, the catalyst can be deactivated, for example with ammonia and/or an aqueous sodium hydroxide solution or an aqueous sulfuric acid solution. The unconverted olefins and the alkanes are then separated from the oligomers by distillation.

The following examples are given by way of illustration and do not limit the invention in any respect.

EXAMPLE 1

An oligomerization reactor comprises two serially arranged reaction stages, each consisting of a 0.25 liter cylindrical steel reactor having a double jacket and a heat regulation by water circulation.

The first stage reactor is continuously fed with a $C_4$ cut whose composition is:

| propane: | 1.1 (% b.w.) |
| --- | --- |
| isobutane: | 6.7 |
| n-butane: | 23.0 |
| 1-butene: | 5.2 |
| trans 2-butene: | 46.4 |
| cis 2-butene: | 17.6 | and with 0.19 g/h of dichloroethylaluminum as a solution in isohexane, 0.054 g/h of a nickel 2-ethylhexanoate solution (11% b.w. nickel content), 0.011 g/h of trifluoroacetic acid and 0.001 g/h of trifluoroacetic anhydride, the latter three components being introduced as a common solution in isohexane. The reactor pressure is maintained at 5 bars by continuous discharge of the reaction product and the temperature at 42° C. by means of a thermostatic bath.

After 4 hours, steady running is observed, corresponding to a 64% conversion of butenes at the outlet of the first stage and 76% at the outlet of the second stage. The products consist essentially of butenes dimers, trimers and tetramers. The yield of dimers, trimers and tetramers is 97%, including the recovered butene.

EXAMPLE 2

This example is not part of the invention and is given by way of comparison.

The apparatus and the operating conditions were the same as in Example No. 1; the $C_4$ cut and the constituents of the catalyst were introduced at the same feed rates, except that trifluoroacetic anhydride was not present.

After 4 hours of run, steady conditions were obtained, the butenes conversion being 57% at the outlet of the first stage and 72% at the outlet of the second stage. The dimers, trimers and tetramers yield, as defined in example No. 1, was 95%.

EXAMPLE 3

The apparatus and the operating conditions were the same as in example No. 1; the $C_4$ cut and the constituents of the catalyst were introduced at the same feed rates, except that trifluoroacetic acid and trifluoroacetic anhydride were introduced at the respective feed rates of 0.001 and 0.008 g/h.

After 4 hours of run, steady conditions were obtained, the butenes conversion being 65% at the outlet of the first stage and 77% at the outlet of the second stage. The yield of dimers, trimers and tetramers, as defined in example No. 1, was 96%.

EXAMPLE 4

The apparatus and the operating conditions were the same as in example No. 1; The $C_4$ cut and the nickel compound were introduced at the same feed rate. 0.23 g/h of dichloroisobutylaluminum as a solution in isohexane, 0.0157 g/h of trichloroacetic acid and 0.00145 g/h of trichloroacetic anhydride were also introduced, the latter two compounds as a solution in isobutane.

After 4 hours of run, steady conditions were obtained, corresponding to a butene conversion of 63% at the outlet of the first stage and 75% at the outlet of the second stage. The dimers, trimers and tetramers yield, as defined in example No. 1, was 96%.

EXAMPLE 5

The apparatus was the same as in example No. 1; the first stage reactor was continuously fed with 80 g/h of a $C_3$ cut of the following composition:

| propane: | 25% b.w. |
| --- | --- |
| propylene: | 75% b.w. | and with 0.053 g/h of ethylaluminum sesquichloride as a solution in isooctane, 0.019 g/h of a solution of nickel 2-ethylhexanoate in isooctane (11% b.w. of nickel), 0.004 g/h of trifluoroacetic acid and 0.00095 g/h of the anhydride of 2-ethylhexanoic acid, the latter two components being introduced simultaneously as a solution in isooctane. The reactor pressure was 15 bars and the temperature 42° C.

After 4 hours of run, steady conditions were obtained, the propylene conversion being 85% at the outlet of the first stage and 94% at the outlet of the second stage. The products consisted essentially of propylene dimers, trimers and tetramers. The yield was 97%, including the recovered propylene.

What is claimed is:

1. In a catalyst composition obtained by contacting, in any order, at least one bivalent nickel compound with at least one hydrocarbylaluminum halide and at least one Bronsted organic acid whose pKa at 20° C. is at most equal to 3, the improvement wherein said hydrocarbylaluminum halide has 1.5–2 halogen atoms per atom of aluminum; and wherein said contacting is effected in the further presence of at least one carboxylic acid anhydride having the formula $(R_3CO)_2O$, wherein each $R_3$ is independently an unsubstituted or halogen-substituted $C_{1-20}$ hydrocarbyl group.

2. A catalyst composition according to claim 1, wherein the Bronsted acid is a halogenocarboxylic acid.

3. A catalyst composition according to claim 1, wherein the Bronsted acid is trifluoroacetic acid, trichloroacetic acid or tribromoacetic acid.

4. A catalyst composition according to claim 1 wherein the anhydride of the carboxylic acid is trifluoroacetic anhydride, trichloroacetic anhydride or tribromoacetic anhydride.

5. A catalyst according to claim 1 wherein the nickel compound has a solubility higher than 1 gram per liter in n-heptane at 20° C.

6. A catalyst composition according to claim 1 wherein the nickel compound is a nickel acetylacetonate or a nickel carboxylate of the formula $(RCOO)_2Ni$, wherein each R is a hydrocarbyl radical having 5 to 20 carbon atoms.

7. A catalyst composition according to claim 1 wherein the hydrocarbylaluminum halide has the formula $AlR_xX_y$, wherein R is hydrocarbyl of 1-12 carbon atoms, X is halogen, x has a value from 1 to 1.5 and y a value from 1.5 to 2 with $x+y=3$.

8. A catalyst composition according to claim 1, wherein the molar ratio of the hydrocarbylaluminum halide to the nickel compound is from 2:1 to 15:1, the molar ratio of the Bronsted acid to the aluminum compound is from 0.01:1 to 0.5:1 and the molar ratio of the anhydride of the carboxylic acid to the nickel compound is from 0.01:1 to 0.5:1.

9. A catalyst composition according to claim 7, wherein said hydrocarbylaluminum halide is ethylaluminum sesquichloride, dichloroethylaluminum or dichloroisobutylaluminum.

10. A catalyst precursor for reaction with a hydrocarbylaluminum halide having 1.5-2 halogen atoms per atom of aluminum to prepare a catalyst composition according to claim 1, said precursor consisting essentially of at least one bivalent nickel compound; at least one Bronsted organic acid whose pKa at 20° C. is at most equal to 3; and at least one carboxylic acid anhydride having the formula $(R_3CO)_2O$, wherein each $R_3$ is independently an unsubstituted or halogen-substituted $C_{1-20}$ hydrocarbyl group; and wherein the molar ratio of the Bronsted acid to the nickel compound is from 0.25:1 to 5:1, and the molar ratio of the anhydride to the nickel compound is from 0.01:1 to 0.5:1.

11. A catalyst precursor according to claim 10, wherein said bivalent nickel compound is a nickel acetylacetonate or a nickel carboxylate of the formula $(RCOO)_2Ni$, wherein each R is a hydrocarbyl radical having 5 to 20 carbon atoms.

12. A catalyst precursor according to claim 10, wherein said Bronsted acid is trifluoroacetic acid, trichloroacetic acid or tribromoacetic acid.

13. A catalyst precursor according to claim 10, wherein said anhydride is trifluoroacetic anhydride, trichloroacetic anhydride or tribromoacetic anhydride.

* * * * *